(12) United States Patent
Rathmacher et al.

(10) Patent No.: US 10,925,845 B2
(45) Date of Patent: Feb. 23, 2021

(54) STABILITY OF VITAMIN D IN β-HYDROXY-β-METHYLBUTYRATE (HMB)

(71) Applicant: Metabolic Technologies, Inc., Ames, IA (US)

(72) Inventors: John Rathmacher, Story City, IA (US); Martin Purpura, Austin, TX (US)

(73) Assignee: Metabolic Technologies, Inc., Ames, IA (US)

( * ) Notice: Subject to any disclaimer, the term of this patent is extended or adjusted under 35 U.S.C. 154(b) by 0 days.

(21) Appl. No.: 16/451,516

(22) Filed: Jun. 25, 2019

(65) Prior Publication Data

US 2019/0388372 A1    Dec. 26, 2019

Related U.S. Application Data

(60) Provisional application No. 62/689,305, filed on Jun. 25, 2018.

(51) Int. Cl.
| | | |
|---|---|---|
| A61K 31/59 | (2006.01) | |
| A61K 31/191 | (2006.01) | |
| A61K 31/045 | (2006.01) | |
| A61K 47/18 | (2017.01) | |
| A61K 47/12 | (2006.01) | |
| A61K 31/205 | (2006.01) | |
| A61K 36/53 | (2006.01) | |
| A61K 47/10 | (2017.01) | |

(52) U.S. Cl.
CPC .......... *A61K 31/191* (2013.01); *A61K 31/045* (2013.01); *A61K 31/205* (2013.01); *A61K 36/53* (2013.01); *A61K 47/10* (2013.01); *A61K 47/12* (2013.01); *A61K 47/183* (2013.01)

(58) Field of Classification Search
CPC ....................................................... A61K 31/59
USPC .................................................. 514/167, 168
See application file for complete search history.

(56) References Cited

U.S. PATENT DOCUMENTS

| | | | |
|---|---|---|---|
| 2006/0019933 A1 | 1/2006 | Boardman et al. | |
| 2013/0171294 A1* | 7/2013 | Martyn ..................... | A23L 2/39 426/2 |
| 2014/0037797 A1 | 2/2014 | Johns et al. | |
| 2016/0184326 A1* | 6/2016 | Rathmacher ............ | A23L 33/30 514/167 |

* cited by examiner

*Primary Examiner* — Raymond J Henley, III
(74) *Attorney, Agent, or Firm* — Emily E. Harris; Matthew W. Coryell

(57) ABSTRACT

The present invention provides a composition comprising an acidic formulation containing β-hydroxy-β-methylbutyrate (HMB), preferably in the free acid form, Vitamin D and a stabilizing excipient, wherein the Vitamin D is stabilized against degradation.

13 Claims, 2 Drawing Sheets

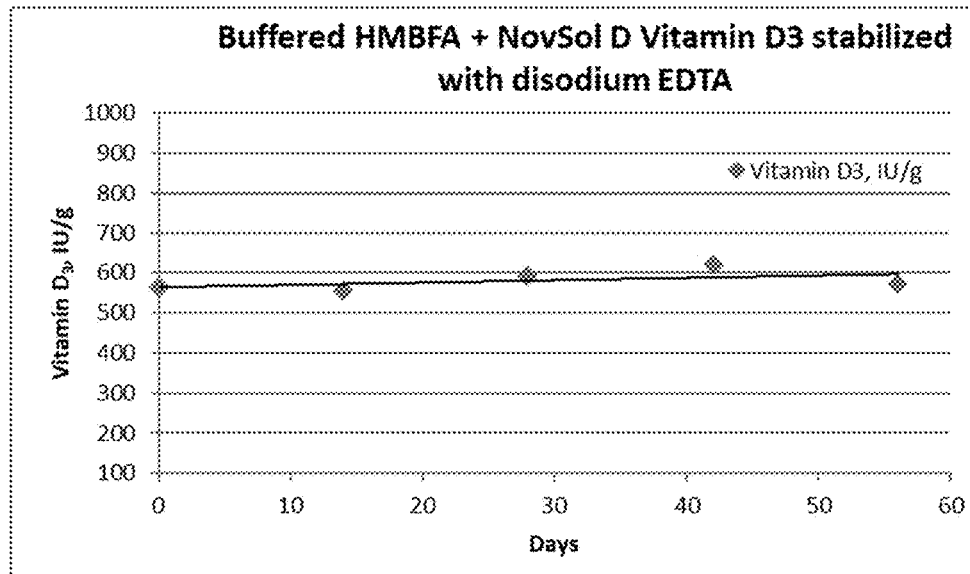

Figure 1. Stability of Vitamin $D_3$ in formula 7 containing buffered HMB free acid + NovaSol D ® protected Vitamin $D_3$(AquaNova, Germany) stabilized with 60 ppm disodium EDTA (Versene™ NA Chelating Agent, Dow Chemical, Midland, MI

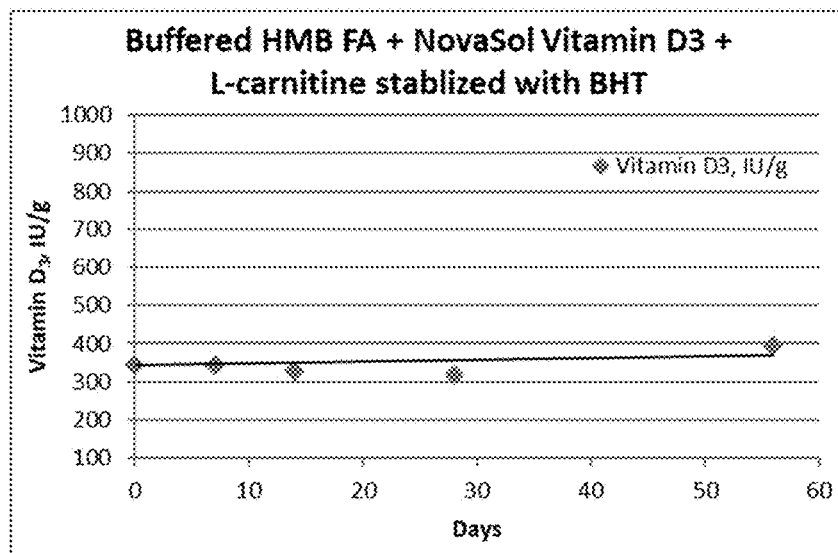

Figure 2. Stability of Vitamin D3 in Formula 10 containing buffered HMBFA + NovaSol D® Vitamin D3(AquaNova, Germany) + L-carnitine stabilized with BHT (Butylated hydroxytoluene, Sigma-Aldrich).

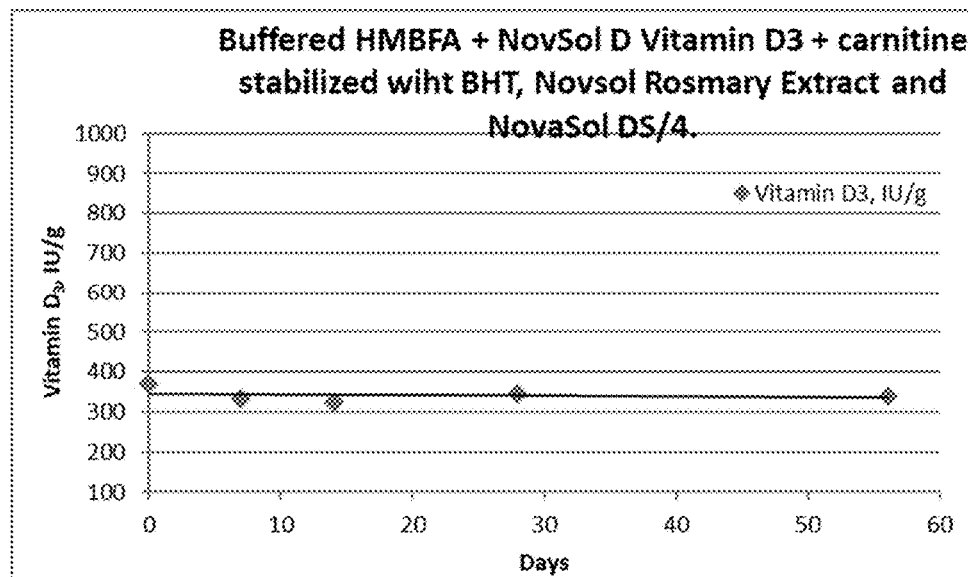
Figure 3. Stability of Vitamin D₃ in formula 11 containing buffered HMBFA + NovaSol D protected Vitamin D₃ + L- carnitine stabilized with NovaSol Rosmary, NovaSol DS/4, and BHT

STABILITY OF VITAMIN D IN β-HYDROXY-β-METHYLBUTYRATE (HMB)

BACKGROUND OF THE INVENTION

This application claims priority to U.S. Provisional Patent Application No. 62/689,305 filed Jun. 25, 2018 and herein incorporates the provisional application by reference.

1. Field

The present invention relates to a composition comprising β-hydroxy-β-methylbutyrate (HMB) and vitamin D. In particular, the present invention relates to compositions containing HMB and vitamin D and methods of stabilizing vitamin D when vitamin D is combined with acidic compositions.

2. Background

Vitamin D has classically been associated with calcium and phosphorous metabolism and bone strength. Until recently, an adequate vitamin D level has been defined using the vitamin D deficiency disease rickets. In recent years vitamin D has been found to have more widespread effects on metabolism other than on calcium and bone structure. Low vitamin D status has been associated with the following: osteoporosis, falls, Type I diabetes, cancer, autoimmune disease, hypertension, periodontal disease, multiple sclerosis, susceptibility/poor response to infection[1].

Vitamin D deficiency is a problem worldwide, as sun exposure has decreased and the use of sunscreen has increased the problem has only been exacerbated. Diet and health can also be mitigating factors on vitamin D levels. Subjects with fat malabsorption syndromes, chronic diseases, on certain medications, or obesity have a higher risk for vitamin D deficiency[2]. Skin tone can also have an effect, as the darker the skin tone, the more time required to produce the same amount of vitamin D. Therefore supplementation is the best way to increase vitamin D and decrease deficiency[2]. Cholecalciferol (Vitamin $D_3$) can be synthesized by humans thru irradiation of 7-dehydrochloesterol in the skin or extracted from lanolin.

Very few naturally occurring foods contain Vitamin D but the flesh of fatty fish and fish liver oils are the best sources. Small amounts of Vitamin D are found in beef liver, dairy products, and each yolk. Some mushrooms provide Vitamin $D_2$ but the amounts are variable. Because Vitamin D is only contained in few foods and often in small amounts, fortification of foods or the supplementation through dietary supplements is necessary. Since the 1930, food and beverage manufactures started fortify foods such as, milk, bread, hot dogs, sodas and even beer. Vitamin D is also available in dietary supplements.

Vitamin $D_3$ is a large and hydrophobic sterol molecule with poor water solubility that is easily degraded by light and oxygen. The stability of vitamin D is excellent in the absence of water, light, acidity, and at low temperatures[3]. The 5,6-trans-isomer and isotachysterol can form when exposed to acid and light[4]. Vitamin is less susceptible to oxidation than vitamin A but oxidation of Vitamin D can be the predominant route for decomposition at the conjugated double bond system at 5,6 and 7,8 position of the secosteroid structure[3]. Vitamin D is quite stable in processes used for fluid milk production or in the production of non-fat dry milk[4]. No significant loss were observed with steam injected at 95° C.[5]. More recently, Vitamin D has been found to be stable in orange juice which has a pH of approximately 4[6]. The bioavailability was equally available as when consumed in capsule forms. However, long-term stability of Vitamin D3 at pH of 4 and lower had not been determined.

HMB

Alpha-ketoisocaproate (KIC) is the first major and active metabolite of leucine. A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB and this accounts for approximately 5% of leucine oxidation. HMB is superior to leucine in enhancing muscle mass and strength. The optimal effects of HMB can be achieved at 3.0 grams per day when given as calcium salt of HMB, or 0.038 g/kg of body weight per day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use. Numerous studies have shown an effective dose of HMB to be 3.0 grams per day as CaHMB (calcium HMB) (~38 mg·kg body weight$^{-1}$·day$^{-1}$). HMB has been tested for safety, showing no side effects in healthy young or old adults. HMB in combination with L-arginine and L-glutamine has also been shown to be safe when supplemented to AIDS and cancer patients.

HMB free acid ("HMBFA"), a delivery form of HMB, has been developed. This delivery form has been shown to be absorbed quicker and have greater tissue clearance than CaHMB. This delivery form is described in U.S. Patent Publication Serial No. 20120053240 which is herein incorporated by reference in its entirety.

HMB has been shown to be effective for increasing muscle mass, increasing strength, and improving muscle function. These effects are most significant when vitamin D levels in the blood are sufficient, which has been further defined to be around at least 25 ng/ml or higher.

Thus, it is desirable to combine HMB with vitamin D in order to maximize the effects of HMB on muscle mass, strength and function. It has been found, however, that vitamin D, and vitamin D3 in particular, is not stable when combined with acidic compositions, including HMB in the free acid form (HMBFA). Vitamin D levels in compositions the solely comprise HMBFA and Vitamin D degrade significantly over time. As HMBFA may be a more effective delivery form of HMB in terms of effect on muscle, it is desirable to combine HMBFA with Vitamin D in order to maximize the efficacy of HMB. Thus, the need exists to develop a stable formulation containing HMBFA and vitamin D. To that end, it has been discovered that Vitamin D is stabilized against degradation in acidic formulations, including formulations containing HMB with the inclusion of at least one stabilization excipient.

SUMMARY OF THE INVENTION

One object of the present invention is to provide a composition containing HMBFA and vitamin D that is stable.

Another object of the present invention is to provide a composition containing HMBFA and vitamin D, wherein the vitamin D does not decrease significantly over time.

These and other objects of the present invention will become apparent to those skilled in the art upon reference to the following specification, drawings, and claims.

The present invention intends to overcome the difficulties encountered heretofore. To that end, a composition comprising HMBFA and vitamin D is provided.

BRIEF DESCRIPTION OF THE DRAWINGS

FIG. 1 depicts the stability of Vitamin D in Formula 7.
FIG. 2 depicts the stability of Vitamin D in Formula 10.
FIG. 3 depicts the stability of Vitamin D in Formula 11.

DETAILED DESCRIPTION OF THE INVENTION

There is disclosed herein formulations for improving the stability of Vitamin D when Vitamin D is combined with HMB. It has been discovered that inclusion of additional components that act as a stabilizing excipient in formulations of HMB and Vitamin D improves the stability of Vitamin D. Representative examples of the stabilizing excipients include but are not limited to EDTA, butylated hydroxytoluene (BHT), carnitine, rosemary extract, carnosolic acid, and/or sorbic acid. The inclusion of at least one of these additives in formulations containing HMB and Vitamin D results in minimal loss of Vitamin D in the formulation over time. The addition of an additive to a formulation containing Vitamin D combined with an acidic components (such as HMBFA), stabilizes the Vitamin D against degradation over time.

Vitamin D is intended to include vitamins $D_2$, $D_3$, and $D_4$ and related analogs.

Stabilizing excipients that are encompassed by this invention include EDTA or antioxidants including BHT, BHA, ascorbyl palmitate, propyl gallate, vitamin E, ascorbic acid, cysteine, methionine, monothioglycerol, sodium thiosulphate, or sulfites.

Vitamin D has been found to degrade significantly over time when Vitamin D is included in acidic formulations. As it is desirable to combine Vitamin D with HMBFA in low pH, acidic formulations, the need exists for stable formulations of HMB and Vitamin D. It was unexpectedly discovered that including a stabilizing excipient, such as EDTA, BHT, carnitine, rosemary extract, carnosolic acid, and/or sorbic acid results in a formulation in which Vitamin D is stabilized against degradation over time.

In most instances, the HMB utilized in clinical studies and marketed as an ergogenic aid has been in the calcium salt form. Recent advances have allowed the HMB to be manufactured in a free acid form for use human and animal uses, and preferably as a nutritional supplement or incorporated into foodstuffs. HMB in the free acid form (HMBFA) has been developed, which was shown to be more rapidly absorbed than CaHMB, resulting in quicker and higher peak serum HMB levels and improved serum clearance to the tissues. The pH of HMBFA is <3.

HMB free acid may therefore be a more efficacious method of administering HMB than the calcium salt form, particularly when administered directly preceding intense exercise. One of ordinary skill in the art, however, will recognize that this current invention encompasses HMB in any form.

HMB in any form may be incorporated into the delivery and/or administration form in a fashion so as to result in a typical dosage range of about 0.5 grams HMB to about 30 grams HMB.

Any suitable dose of HMB can be used within the context of the present invention. Methods of calculating proper doses are well known in the art.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, vitamins, proteins, peptides, carbohydrates, fats, sugars, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water.

The composition of the dietary supplement may be a powder, a gel, a liquid or may be tabulated or encapsulated, for instance in a softgel formulation. The following examples examined the stability of Vitamin D when combined with HMB in a softgel or capsule delivery form. The invention is not limited to any particular delivery form, and can include combinations of HMB and Vitamin D in liquid formulations, gels and foodstuffs.

Although any suitable pharmaceutical medium comprising the composition can be utilized within the context of the present invention, preferably, the composition is combined with a suitable pharmaceutical carrier, such as dextrose or sucrose.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, glucose, peptides, proteins and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The composition can be administered over an extended period of time, such as weeks, months or years.

Any suitable dose of HMB and vitamin D can be used within the context of the present invention. Methods of calculating proper doses are well known in the art.

The term administering or administration includes providing a composition to a mammal, consuming the composition and combinations thereof.

Experimental Example

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

The objective of the following experiment was to test the stability of Vitamin $D_3$ in HMBFA in different formulas. A loss of Vitamin $D_3$ less than 10% was considered acceptable Methods: Eleven different HMBFA/Vitamin $D_3$ formulas were tested. These formulas were tested for the stability of Vitamin $D_3$ over time. The formulas were as follows:

1. HMBFA+Vitamin D3 (100 HP, BASF, Denmark)
2. Vitamin D3 (100 HP, BASF, Denmark) in HMB FA plus Choline Chloride (Acros Organics)
3. Vitamin $D_3$ (100 HP, BASF, Denmark) in HMB FA plus Betaine (Sigma-Aldrich)
4. Buffered HMBFA+Vitamin $D_3$ (100 HP, BASF, Denmark)
5. Buffered HMBFA+BASF protected Vitamin D3 (100 GFP/HP, BASF, Denmark)
6. HMBFA+NovaSol D®, protected Vitamin $D_3$ (AquaNova®, Germany)
7. Buffered HMB free acid+NovaSol D® protected Vitamin $D_3$(AquaNova, Germany) stabilized with 60 ppm disodium EDTA (Versene™ NA Chelating Agent, Dow Chemical, Midland, Mich.),
8. HMBFA+NovaSol D® Vitamin $D_3$ (AquaNova, Germany) stabilized with 60 ppm disodium EDTA (Versene™ NA Chelating Agent, Dow Chemical, Midland, Mich.)
9. Buffered HMBFA+Vitamin $D_3$ (Sigma-Aldrich) stabilized with 60 ppm disodium EDTA (Versene™ NA Chelating Agent, Dow Chemical, Midland, Mich.)
10. Buffered HMBFA+NovaSol D® Vitamin $D_3$(AquaNova, Germany)+L-carnitine stabilized with BHT (Butylated hydroxytoluene, Sigma-Aldrich)
11. Buffered HMBFA+NovaSol D® Vitamin D3 (AquaNova, Germany)+L-carnitine stabilized with NovaSol Rosemary®, NovaSol DS/4®, and BHT (Butylated hydroxytoluene, Sigma-Aldrich)

Vitamin D3 was measured by HPLC by Heartland assays.

Results: Of the 11 formula tested, formula 7 containing buffered HMBFA plus NovaSol D protected Vitamin D3 stabilized with 60 ppm disodium EDTA (Versene™ NA), formula 10 containing HMBFA plus NovaSol D protected Vitamin D3 stabilized with BHT, and formula 11 Buffered HMBFA+NovaSol D Vitamin D3 stabilized with NovaSol Rosemary, NovaSol DS/4, and BHT were stable. The percent chance in Vitamin D3 is presented in the following table:

TABLE 1

| Formula No. | | days | Vit. D3, % change |
|---|---|---|---|
| 1 | HMBFA + vitamin $D_3$ | 28 | −57% |
| 2 | Vitamin $D_3$ in HMBFA plus Choline Chloride | 14 | −28% |
| 3 | Vitamin $D_3$ in HMBFA plus Betaine | 14 | −28% |
| 4 | Buffered HMBFA acid + Vitamin $D_3$ | 28 | −61% |
| 5 | Buffered HMBFA + BASF protected Vitamin $D_3$ | 35 | −35% |
| 6 | HMB FA + NovaSol D protected Vitamin $D_3$ | 35 | −32% |
| 7 | Buffered HMB free acid + NovaSol Dprotected Vitamin $D_3$ stabilized with 60 ppm disodium EDTA | 56 | 2% |
| 8 | HMBFA + NovaSol D protected Vitamin $D_3$ stabilized with 60 ppm disodium EDTA | 14 | −32% |
| 9 | Buffered HMBFA + Sigma Vitamin $D_3$ stabilized with 60 ppm disodium EDTA | 28 | −11% |
| 10 | Buffered HMBFA + NovaSol D protected Vitamin $D_3$ + L-carnitine stabilized with BHT | 56 | 14.9 |
| 11 | Buffered HMBFA + NovaSol D protected Vitamin $D_3$ + L-carnitine stabilized with NovaSol Rosmary, NovaSol DS/4, and BHT | 56 | −7.9 |

FIGS. 1, 2, and 3 illustrate the stability of Vitamin D3 in formula 7, 10, and 11, respectively. In conclusion, these studies demonstrate that vitamin $D_3$ is stable when formulated with buffered HMBFA and disodium EDTA or when BHT is substituted for disodium EDTA. A protected vitamin $D_3$ such as NovaSol D is also necessary.

Preparation of Buffered HMB in the Free Acid Form (HMBFA)

Briefly, 400 g HMBFA (TSI lot 12111036) was weigh into a one liter beaker and then 37.8 g of with potassium carbonate ($K_2CO_3$) was added to the HMBFA. A stir bar was added and the mixture was stirred for 60 h. The resulting pH was approximately 4.5. Alternatively, the reaction may be accelerated by mixing water (35 g) with potassium carbonate (37) g and then adding HMBFA (400 g).

The vitamin D3 in formula 7 was from AquaNova and is described as NovaSOL D. This vitamin D3 product is protected with Polysorbate 80. The product is water and oil soluble, resulting in a clear solution. To calculate the amount of the component's needed, the following was used: to use per capsule 250 IU Vitamin D3 (Calculation 1 µg=40 IU), meaning 6.25 µg based on this 0.25% NovaSOL D product requires 2.5 mg per capsule of NovaSOL D.

The EDTA used in formula 7 and formula 8 was Dow's disodiumEDTA (Versene™ NA Chelating Agent, Dow Chemical, Midland, Mich. In formula, 10 and 11 disodium EDTA was replaced with the preservative BHT. In addition, formula 11 also contained the antioxidant NovaSol rosemary extract which is high in carnosolic acid and the preservative NovaSol DS/4 (sorbic acid).

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

REFERENCES

1 Heaney, R. P. Vitamin D in Health and Disease. *Clin. J. Am. Soc. Nephrol* 3, 1535-1541 (2008).
2 Holick, M. F. et al. Evaluation, treatment, and prevention of vitamin D deficiency: an Endocrine Society clinical practice guideline. *J Clin Endocrinol Metab* 96, 1911-1930, doi:10.1210/jc.2011-0385 (2011).
3 Eitenmiller, R. R. L. J., W. O.; in *Vitamin Analysis for the Health of Food Sciences* 77-107 (CRC Press, 1998).
4 Renken, S. A. W., J. J. Vitamin stability in milk. *Food Sci* 58, 552-556 (1993).
5 Indyk, H. E. L., V.; Woollard, d.C. Solubility of vitamin $D_3$ during spray-dying of milk. *Food Chem* 57, 283-286 (1996).
6 Biancuzzo, R. M. et al. Fortification of orange juice with vitamin D(2) or vitamin D(3) is as effective as an oral supplement in maintaining vitamin D status in adults. *Am J Clin Nutr* 91, 1621-1626, doi:10.3945/ajcn.2009.27972 (2010).

The invention claimed is:

1. A stable acidic formulation comprising β-hydroxy-β-methylbutyrate (HMB) in the free acid form, vitamin D and at least one stabilizing excipient, wherein vitamin D is stabilized against degradation over time.
2. The formulation of claim 1, wherein the stabilizing excipient is selected from the list consisting of EDTA, butylated hydroxytoluene (BHT), carnitine, rosemary extract, carnosolic acid, and sorbic acid.
3. The formulation of claim 1, wherein the stabilizing excipient is selected from the list consisting of EDTA and butylated hydroxytoluene (BHT).
4. The formulation of claim 1, wherein the formulation is contained within a delivery form selected from the list consisting of a capsule, a softgel, a liquid, and a foodstuff.
5. A method of stabilizing vitamin D in an acidic formulation, comprising the step of including at least one stabilization excipient in a formulation containing vitamin D and β-hydroxy-β-methylbutyrate (HMB) to result in the stabilization of the vitamin D against degradation over time.
6. The method of claim 5, wherein the HMB is the free acid form.
7. The method of claim 5, wherein the stabilization excipient is selected from the list consisting of EDTA, butylated hydroxytoluene (BHT), carnitine, rosemary extract, carnosolic acid, and sorbic acid.
8. A method of minimizing degradation of vitamin D in an acidic formulation containing β-hydroxy-β-methylbutyrate (HMB) and vitamin D comprising the step of including at least one stabilization excipient in said formulation, wherein the stabilization excipient protects the vitamin D from degradation.
9. The method of claim 8 wherein the HMB is the free acid form.
10. The method of claim 8, wherein the stabilization excipient is selected from the list consisting of EDTA, butylated hydroxytoluene (BHT), carnitine, rosemary extract, carnosolic acid, and sorbic acid.
11. The method of claim 9, wherein the formulation is contained within a delivery form selected from the list consisting of a capsule and a softgel.
12. The method of claim 8, wherein the vitamin D degrades in an amount that is less than around 10%.
13. The method of claim 12, wherein the degradation of vitamin D is less than around 10% at thirty days.

* * * * *